(12) United States Patent
Ebenbeck et al.

(10) Patent No.: US 6,916,839 B2
(45) Date of Patent: Jul. 12, 2005

(54) PYRAZOLYLARYLALKINES

(75) Inventors: Wolfgang Ebenbeck, Leverkusen (DE); Florian Rampf, Köln (DE); Albrecht Marhold, Leverkusen (DE)

(73) Assignee: Bayer Chemicals Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/751,622

(22) Filed: Jan. 5, 2004

(65) Prior Publication Data

US 2004/0142820 A1 Jul. 22, 2004

(30) Foreign Application Priority Data

Jan. 7, 2003 (DE) .......................................... 103 00 123

(51) Int. Cl.[7] .................. A61K 31/415; A61K 31/4427; C07D 231/16; C07D 231/10; C07D 213/02
(52) U.S. Cl. ........................ 514/406; 514/403; 514/341; 546/275.4; 548/366.1; 548/377.1
(58) Field of Search ........................ 548/366.1; 514/406, 514/341; 546/275.4

(56) References Cited

U.S. PATENT DOCUMENTS

| 5,300,521 A | 4/1994 | Eberle et al. ................ 514/406 |
| 2002/0156115 A1 | 10/2002 | Oda et al. .................... 514/407 |
| 2003/0191171 A1 | 10/2003 | Oda et al. .................... 514/406 |
| 2003/0199565 A1 * | 10/2003 | Kalindjian et al. ......... 514/381 |

OTHER PUBLICATIONS

Eugene Tretyakov, "Peculiarities of copper(I) and palladium-catalyzed cross-coupling of terminal alkynes with vicinal amino- and (N-acetylamino)-iodopyrazoles. Synthesis of alkynylaminopyrazoles," May 11, 1999, J. Chem. Soc., Perkin Trans. 1, p. 3713–3720.*

* cited by examiner

*Primary Examiner*—Joseph K. McKane
*Assistant Examiner*—Susannah E. Lee
(74) *Attorney, Agent, or Firm*—Diderico van Eyl

(57) ABSTRACT

The present invention relates to pyrazolylarylalkines and to their use, to a process for preparing pyrazolylarylalkines and also to intermediates.

24 Claims, No Drawings

PYRAZOLYLARYLALKINES

BACKGROUND OF THE INVENTION

1. Field of the Invention

The present invention relates to pyrazolylarylalkines and to processes for preparing and using pyrazolylarylalkines, and also to their intermediates.

2. Brief Description of the Prior Art

Pyrazolylarylalkines have gained industrial significance in particular as intermediates for the preparation of insecticides and acaricides (see also EP-A 571 326 and EP-A 1 219 173). While processes for preparing pyrazolylarylalkines are generally known, these processes are disadvantaged as described below. Illustratively, 4-pyrazolyl-phenylalkines can be prepared, for example, by palladium-catalysed coupling of phenylalkines with iodopyrazoles. This process is however, disadvantaged in that some phenylalkines, for example 3,5-bis(trifluoromethyl)phenylalkine, tend to be susceptible to spontaneous and uncontrolled decomposition. The process is further disadvantaged in that iodopyrazoles can only be obtained in moderate yields by iodinating the corresponding pyrazoles.

There is therefore a need for a process which, starting from reactants which are available easily and in good yield, enables the reliable preparation of pyrazolylalkines.

SUMMARY OF THE INVENTION

A process has now been found for preparing compounds of the formula (I):

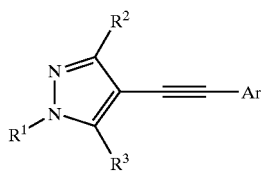

(I)

in which $R^1$ is hydrogen, $C_1$–$C_{12}$-alkyl, $C_5$–$C_{14}$-aryl, $C_6$–$C_{15}$-arylalkyl, $C_1$–$C_{12}$-fluoroalkyl or radicals of the formula (II):

(C$_1$–C$_8$-alkylene)-B—D—E (II)

and $R^2$ and $R^3$ are each independently hydrogen, $C_1$–$C_{12}$-alkyl, $C_1$–$C_{12}$-alkoxy, $C_5$–$C_{14}$-aryl, $C_5$–$C_{14}$-aryloxy, $C_6$–$C_{15}$-arylalkyl, $C_6$–$C_{15}$-arylalkoxy, chlorine, fluorine, cyano, free or protected formyl, $C_1$–$C_{12}$-fluoroalkyl, $C_1$–$C_{12}$-fluoroalkylthio, $C_1$–$C_{12}$-fluoroalkoxy or radicals of the formulae (IIIa) to (IIIf):

| A—B—D—E | (IIIa) | A—E | (IIIb) |
|---|---|---|---|
| A—SO$_2$—E | (IIIc) | A—B—SO$_2$R$^5$ | (IIId) |
| A—SO$_3$W | (IIIe) | A—COW | (IIIf) | where, in the formulae (II) and (IIIa) to (IIIf),

A is absent or is a $C_1$–$C_8$-alkylene, $C_1$–$C_8$-alkenylene or $C_1$–$C_8$-fluoroalkylene radical and B is absent or is oxygen, sulphur or NR$^4$
where $R^4$ is hydrogen, $C_1$–$C_8$-alkyl, $C_6$–$C_{15}$-arylalkyl or $C_5$–$C_{14}$-aryl and D is a carbonyl group and E is $R^5$, OR$^5$, NHR$^6$ or N(R$^6$)$_2$,
where $R^5$ is $C_1$–$C_8$-alkyl, $C_6$–$C_{15}$-arylalkyl or $C_5$–$C_{14}$-aryl and $R^6$ is in each case independently $C_1$–$C_8$-alkyl, $C_6$–$C_{15}$-arylalkyl or $C_6$–$C_{14}$-aryl, or N(R$^6$)$_2$ together is a cyclic amino radical having 4 to 12 carbon atoms and W is OH, NH$_2$ or OM where M is an alkali metal ion, half an equivalent of an alkaline earth metal ion, an ammonium ion or an organic ammonium ion and Ar is a mono-, bi- or tricyclic aromatic radical having a total of 5 to 18 ring atoms, and in which at most one ring atom per cycle is selected from the group of oxygen, sulphur and nitrogen, and the mono-, bi- or tricyclic aromatic radical is optionally mono- or polysubstituted, which is characterized in that in one step, a), the compounds of the formula (IV)

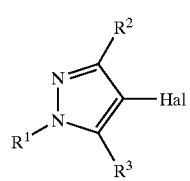

(IV)

in which $R^1$, $R^2$ and $R^3$ are each independently as defined above and Hal is chlorine, bromine or iodine are converted by reacting with compounds of the formula (V)

(V)

in which $R^7$ is hydrogen, halogen, Ar or COOR$^8$ where $R^8$ is $C_1$–$C_8$-alkyl, $C_5$–$C_{14}$-aryl or $C_6$–$C_{15}$-arylalkyl, in the presence of a catalyst to compounds of the formula (VI):

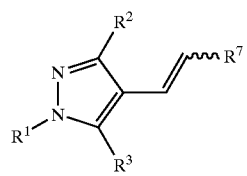

(VI)

in which $R^1$, $R^2$, $R^3$ and $R^7$ are each independently as defined above, and in one step, b), I) in the case that $R^7$ is hydrogen, halogen or COOR$^8$, i) the compounds of the formula (VI), optionally after halogenation, are converted by elimination to compounds of the formula (VII):

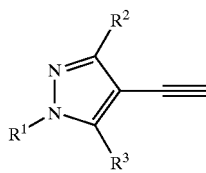

(VII)

in which
R¹, R² and R³ are each independently as defined above and ii) the compounds of the formula (VII) are converted to compounds of the formula (I) by reacting with compounds of the formula (VIII):

Hal-A    (VIII)

in which
Ar is as defined above and
Hal is chlorine, bromine or iodine, in the presence of a catalyst, II) and in the case that R⁷ is Ar, the compounds of the formula (VI) are converted to compounds of the formula (I) by halogenating and eliminating.

In the context of the invention, all radical definitions, parameters and illustrations specified above and listed hereinbelow, in general or within areas of preference, i.e. the particular areas and areas of preference, may be combined as desired.

DETAILED DESCRIPTION OF THE INVENTION

Alkyl, alkoxy, alkylene and alkenylene are in each case independently a straight-chain, cyclic, branched or unbranched alkyl, alkoxy, alkylene or alkenylene radical respectively, each of which may optionally be further substituted by $C_1$-$C_4$-alkoxy. The same applies to the nonaromatic moiety of an arylalkyl radical.

$C_1$-$C_4$-Alkyl is, for example, methyl, ethyl, n-propyl, isopropyl, n-butyl, sec-butyl and tert-butyl, $C_1$-$C_8$-alkyl is additionally, for example, n-pentyl, 1-methylbutyl, 2-methylbutyl, 3-methylbutyl, neopentyl, 1-ethylpropyl, cyclohexyl, cyclopentyl, n-hexyl, 1,1-dimethylpropyl, 1,2-dimethyl-propyl, 1-methylpentyl, 2-methylpentyl, 3-methylpentyl, 4-methylpentyl, 1,1-dimethylbutyl, 1,2dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl and n-octyl, and $C_1$-$C_{12}$-alkyl is further additionally, for example, adamantyl, the isomeric menthyls, n-nonyl, n-decyl and n-dodecyl.

$C_1$-$C_4$-Alkoxy is, for example, methoxy, ethoxy, n-propoxy, isopropoxy, n-butoxy, sec-butoxy and tert-butoxy, $C_1$-$C_8$-alkoxy is additionally n-pentoxy, 1-methylbutoxy, 2-methylbutoxy, 3-methyl-butoxy, neopentoxy, 1-ethylpropoxy, cyclohexoxy, cyclo-pentoxy, n-hexoxy and n-octoxy, and $C_1$-$C_{12}$-alkoxy is further additionally, for example, adamantoxy, the isomeric menthoxy radicals, n-decoxy and n-dodecoxy.

$C_1$-$C_8$-Alkylene is, for example, methylene, 1,1-ethylene, 1,2-ethylene, 1,1-propylene, 1,3-propylene 1,4-butylene, 1,2-cyclohexoxylene and 1,2-cyclopentylene.

$C_2$-$C_8$-Alkenylene is, for example, 1,1-ethenylene, 2-ethoxy-1,1-ethenylene and 2-methoxy-1,1-ethenylene.

Fluoroalkyl and fluoroalkylene are in each case independently a straight-chain, cyclic, branched or unbranched alkyl radical and alkylene radical respectively, each of which is singly, multiply or fully substituted by fluorine atoms and is in addition optionally singly or multiply substituted by chlorine atoms.

For example, $C_1$-$C_{12}$-fluoroalkyl is trifluoromethyl, chlorodifluoromethyl, 2,2,2-trifluoroethyl, pentafluoroethyl, nonafluorobutyl, heptafluoroisopropyl, perfluorooctyl, perfluorododecyl and perfluorohexadecyl.

Aryl is in each case independently a heteroaromatic radical having 5 to 14 framework carbon atoms of which no, one, two or three framework carbon atoms per cycle, but at least one framework carbon atom in the entire molecule, may be substituted by heteroatoms selected from the group of nitrogen, sulphur and oxygen, or preferably a carbocyclic aromatic radical having 6 to 14 framework carbon atoms.

Examples of carbocyclic aromatic radicals having 6 to 14 framework carbon atoms are phenyl, biphenyl, naphthyl, phenanthrenyl, anthracenyl or fluorenyl and heteroaromatic radicals having 5 to 14 framework carbon atoms of which no, one, two or three framework carbon atoms per cycle, but at least one framework carbon atom in the entire molecule, may be substituted by heteroatoms selected from the group of nitrogen, sulphur and oxygen are, for example, pyridinyl, oxazolyl, benzofuranyl, dibenzofuranyl or quinolinyl.

In addition, the carbocyclic aromatic radical or heteroaromatic radical may be substituted by up to five identical or different substituents per cycle which are selected from the group of nitro, cyano, chlorine, fluorine, $C_1$-$C_{12}$-alkyl, $C_1$-$C_{12}$-fluoroalkyl, $C_1$-$C_{12}$-fluoroalkoxy, $C_1$-$C_{12}$-fluoroalkylthio, $C_1$-$C_{12}$-alkoxy, di($C_1$-$C_8$-alkyl)amino, tri($C_1$-$C_6$-alkyl)siloxyl or radicals of the formulae (IIIa) to (IIIf) as defined above.

Arylalkyl is in each case independently a straight-chain, cyclic, branched or unbranched alkyl radical as defined above which may be singly, multiply or filly substituted by aryl radicals as defined above.

The preferred substitution patterns are defined hereinbelow:

R¹ is preferably hydrogen, phenyl or $C_1$-$C_4$-alkyl, more preferably methyl.

R² is preferably $C_1$-$C_{12}$-fluoroalkyl, more preferably trifluoromethyl, chlorodifluoromethyl, 2,2,2-trifluoroethyl, pentafluoroethyl, nonafluorobutyl, heptafluoroisopropyl, perfluorooctyl, perfluorododecyl and perfluorohexadecyl, and even greater preference is given to trifluoro-methyl.

R³ is preferably hydrogen, $C_1$-$C_4$-alkyl, $C_5$-$C_{14}$-aryl or the following radicals which can be encompassed by the formulae (IIIa) to (IIIf):

—$CH_2CN$, —$CH_2COO(C_1$-$C_8$-alkyl), —$CH_2COO(C_5$-$C_{14}$-aryl), —$CH_2CONH(C_1$-$C_8$alkyl), —$CH_2CON(C_1$-$C_8$-alkyl)_2$, —$C(=CHOCH_3)COO(C_1$-$C_8$-alkyl), $C(=CHOCH_3)$ $COO(C_5$-$C_{14}$-aryl), —$C(=CHOCH_3)CONH(C_1$-$C_8$-alkyl), and —$C(=CHOCH_3)CON(C_1$-$C_8$-alkyl)_2$.

R³ is more preferably $C_1$-$C_4$-alkyl or —$CH_2COO(C_1$-$C_8$-alkyl), and even greater preference is given to methyl.

Ar is preferably a phenyl or pyridyl radical which is non-, mono-, di- or trisubstituted by radicals which are selected from the group of nitro, cyano, chlorine, fluorine, $C_1$-$C_{12}$-alkyl, $C_1$-$C_{12}$-fluoroalkyl, $C_1$-$C_{12}$-fluoroalkoxy, $C_1$-$C_{12}$-fluoroalkylthio, $C_1$-$C_{12}$-alkoxy, di($C_1$–$C_8$-alkyl)amino, tri($C_1$–$C_6$-alkyl)siloxyl or radicals of the formulae (IIIa) to (IIIf) as defined above.

Ar is more preferably a phenyl radical which is non-, mono-, di- or trisubstituted by radicals which are selected from the group of chlorine, fluorine, $C_1$–$C_{12}$-alkyl, $C_1$–$C_{12}$-fluoroalkyl, $C_1$–$C_{12}$-fluoroalkoxy, $C_1$–$C_{12}$-fluoroalkylthio or $C_1$–$C_{12}$-alkoxy.

Ar is even more preferably a phenyl radical which is mono-, di- or trisubstituted by radicals which are selected from the group of fluorine, $C_1$–$C_4$-alkyl, $C_1$–$C_4$-fluoroalkyl, $C_1$–$C_4$-fluoroalkoxy or $C_1$–$C_4$-fluoroalkylthio, and greater preference is given to fluorine, trifluoromethyl, trifluoromethoxy and trifluoromethylthio, and even greater preference to trifluoromethyl.

Very particularly preferred Ar radicals include:
3,5-bis(trifluoromethyl)phenyl, 2,4-bis(trifluoromethyl)phenyl, 3,4-bis(trifluoromethyl)phenyl, 3-methyl-5-(triflusoromethyl)phenyl, 4-methyl-3-(trifluoromethyl)phenyl and 2-methyl-5-(trifluoromethyl)phenyl.

$R^7$ is preferably hydrogen, bromine, chlorine, COO-methyl, COO-ethyl, COO-phenyl, COO-isopropyl and COO-tert-butyl.

A very particularly preferred compound of the formula (I) is 4-ethinyl-1,5-dimethyl-3-(trifluoromethyl)-1H-pyrazolyl-3,5-bis(trifluoromethyl)benzene.

In step a) compounds of the formula (IV) are converted to compounds of the formula (VI) by reacting with compounds of the formula (V) in the presence of a catalyst. The compounds of the formula (V) are known from the literature or can be synthesized in a similar manner to literature methods. In one embodiment of the process according to the invention, the compounds of the formula (V) in which $R^7$ is Ar can also be obtained by reacting ethylene with compounds of the formula (Va):

Ar—Y (Va)

in which
Y is chlorine, bromine, iodine or a sulfonate and.
Ar is as defined above, in the presence of a catalyst, in which case in particular the areas of preference described hereinbelow for catalysts, reaction parameters and base apply and the further coupling in step a) is effected without intermediate isolation of the compound of the formula (V).

The compounds of the formula (VI) as particularly valuable intermediates are likewise encompassed by the invention. This applies both to the pure cis- and trans-configured compounds of the formula (VI) and for any mixtures thereof. The above-specified areas of preference apply correspondingly.

Compounds of the formula (VI) include:
4-ethenyl-1,5-dimethyl-3-(trifluoromethyl)-1H-pyrazolyl-3,5-bis(trifluoromethyl)]benzene, 4-ethenyl-1,5-dimethyl-3-(trifluoromethyl)-1H-pyrazole, 4-(2-chloroethenyl)-1,5-dimethyl-3-(trifluoromethyl)-1H-pyrazole, 4-(2-bromoethenyl)-1,5-dimethyl-3-(trifluoromethyl)-1H-pyrazole, 4-(2-methoxycarbonylethenyl)-1,5-dimethyl-3-(trifluoromethyl)-1H-pyrazole, 4-(2-ethoxycarbonylethenyl)-1,5-dimethyl-3-(trifluoromethyl)-1H-pyrazole and 4-(2-isopropoxycarbonylethenyl)-1,5-dimethyl-3-(trifluoromethyl)-1H-pyrazole.

Some of the compounds of the formula (IV) in which Hal is iodine and which are used as reactants are known from the literature or can be synthesized in a similar manner to the literature.

Compounds of the formula (IV) in which Hal is bromine or chlorine as preferred reactants are likewise encompassed by the invention and are obtainable, for example, by reacting compounds of the formula (IX)

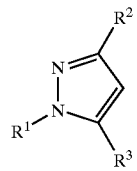

(IX)

in which
$R^1$, $R^2$ and $R^3$ are each independently as defined above with bromine, chlorine or interhalogen compounds of bromine and chlorine in the presence of an acid having a pKa value of 3 or less, preferably 0 or less.

Compounds of the formula (IV) include: 4-bromo-1,5-dimethyl-3-(trifluoromethyl)-1H-pyrazole, and 4-chloro-1,5-dimethyl-3-(trifluoromethyl)-1H-pyrazole.

Halogenations according to step b) are necessary when, in the case I), $R^7$ is hydrogen or $COOR^8$, or in the case II).

These halogenations can be effected in a manner known per se, for example by reacting the particular compounds of the formula (VI) with bromine, chlorine or interhalogen compounds of bromine and chlorine, sulphonyl chloride or bromide or phosphorus pentachloride or pentabromide, optionally in the presence of an organic solvent which is at least 90% inert under the reaction conditions. Preference is given to the use of chlorine or bromine, particular preference to the use of bromine.

Such organic solvents may in particular be:
aliphatic, alicyclic or aromatic, optionally halogenated hydrocarbons, for example benzine, benzene, toluene, xylene, chlorobenzene, dichlorobenzene, petroleum ether, hexane, cyclohexane, dichloromethane, chloroform or carbon tetrachloride.

The reaction temperature in the halogenations may be, for example, –20 to 150° C., preferably 20 to 100° C., and the reaction pressure, for example, 0.5 to 100 bar, preferably 0.9 to 5 bar, and even greater preference is given to ambient pressure.

The halogenations result in compounds of the formula (VIa) which are likewise encompassed by the invention in the totality of the possible stereoisomers. These are in particular the (R)-* 1-(S)-*2-, (R)-*1-(R)-*2-, (S)-*1-(S)-*2- and (S)-* I-(R)-*2-isomers. In the formula (VIa),

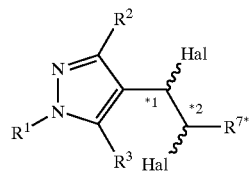

(VIa)

$R^1$, $R^2$ and $R^3$ are each as defined above, including the areas of preference specified and
$R^{7*}$ is as defined above, including the areas of preference specified for $R^7$, but excluding the definition of halogen for $R^{7*}$, and Hal is in each case independently bromine or chlorine, more preferably chlorine.

Preferred compounds of the formula (VIa) include:
4-(1,2-dichloroethyl)-1,5-dimethyl-3-(trifluoromethyl)-1H-pyrazole, 4-(1,2-dibromoethyl)-1,5-dimethyl 3-(trifluoromethyl)-1H-pyrazole, 4-(1-bromo-2-chloroethyl)-1,5-dimethyl-3-(trifluoromethyl)-1H-pyrazole, 4-(2-bromo-1-chloroethyl)-1,5-dimethyl-3-(trifluoromethyl)-1H-pyrazole, 4-(2-methoxycarbonyl-1,2-dibromoethyl)-1,5-dimethyl-3-(trifluoromethyl)-1H-pyrazole, 4-(2-methoxycarbonyl-1,2-dichloroethyl)-1,5-dimethyl-3-(trifluoromethyl)-1H-pyrazole, 4-(2-ethoxycarbonyl-1,2-dibromoethyl)-1,5-dimethyl-3-(trifluoromethyl)-1H-pyrazole and 4-(2-ethoxycarbonyl-1,2-dichloroethyl)-1,5-dimethyl-3-(trifluoromethyl)-1H-pyrazole.

Eliminations according to step b) are necessary in the case I) or in the case II).

The eliminations can be carried out in an organic solvent in the presence of base.

Suitable organic solvents for the elimination are, for example: ethers such as dioxane, tetrahydrofuran or ethylene glycol dimethyl or diethyl ether; alcohols such as methanol, ethanol and isopropanol; sulphones such as tetramethylenesulphone, and sulphoxides such as dimethyl sulphoxide, and preference is given to dimethyl sulphoxide. It is also possible, where appropriate, to work in a biphasic mixture, in which case it may be advantageous to add phase transfer catalysts. Such a biphasic mixture consists, for example, of aqueous potassium hydroxide solution, toluene and PEG 600.

The bases used may be, for example:

alkaline earth metal or alkali metal hydrides, hydroxides, amides, alkoxides, for example sodium hydride, sodium amide, lithium diethylamide, sodium methoxide, sodium ethoxide, potassium tert-butoxide, sodium hydroxide, potassium hydroxide, tertiary amines such as trimethylamine, triethylamine, tributylamine, diisopropylethylamine, piperidine, N-methylpiperidine, N,N-dimethylaminopyridine, diazabicyclooctane (DABCO), diazabicyclononene (DBN) or diazabicycloundecene (DBU) and also N-heteroaromatic compounds, for example pyridine and 3-N,N-dimethylaminopyridine.

Especially for the elimination of chloroethenyl compounds, combinations of organolithium compounds in various ethers, hydrides and amides in ammonia, dimethyl sulphoxide or liquid ammonia and potassium tert-butoxide in various ethers have been found to be useful.

The eliminations can be carried out, for example, at temperatures of −20 to 200° C., preferably at 20 to 180° C., more preferably at 80 to 180° C.

The reaction time may be, for example, 0.5 to 72 hours, preferably 2 to 24 hours.

The pressure in the elimination is uncritical and may be, for example, 0.5 to 100 bar, preferably 0.8 to 3 bar. Particular preference is given to ambient pressure.

In a preferred embodiment, when the elimination is preceded by halogenation, an intermediate isolation and/or purification of the compounds of the formula (VIa) can be dispensed with.

In step b) in variant i), compounds of the formula (VII) are obtained which are likewise encompassed by the invention. The areas of preference for $R^1$, $R^2$ and $R^3$ specified above apply correspondingly.

A particularly preferred compound of the formula (VII) is: 4-ethinyl-1,5-dimethyl-3-(trifluoromethyl)-1H-pyrazole.

Preferred catalysts are catalysts which contain palladium.

In a preferred embodiment, in the case of the reactions in the presence of catalyst, base is also added, and in the case of conversions of alkines, preference is given to additionally adding copper salt.

The catalysts containing palladium which are used are, for example and with preference, palladium complexes.

Palladium complexes can be generated, for example, in the reaction solution from palladium compounds and ligands, or in the form of already isolated palladium complexes, and preference is given to generating palladium complexes in the reaction solution.

Isolated palladium complexes which are suitable for the process according to the invention are, for example, palladium complexes which contain, as ligands, phosphorus compounds, for example phosphines, phosphites, phosphonites or mixtures thereof, preferably phosphines.

The palladium complexes which may contain phosphorus compounds as ligands are, for example and with preference, those of the formula (Xa):

$$[PdL^1{}_2An_2] \tag{Xa}$$

in which $L^1$ is in each case a monophosphorus compound or $L^1{}_2$ together is a diphosphorus compound and An is an anion, preferably chloride, bromide, iodide, acetate, propionate, allyl or cyclopentadienyl, or those of the formula (Xb):

$$[PdL^2{}_n] \tag{Xb}$$

in which n is 2, 3 or 4 and in which $L^2$ may in each case be a monophosphorus compound or half an equivalent of a diphosphorus compound.

Monophosphorus compounds are, for example and with preference, those of the formula (XIa):

$$P(G-R^9)_3 \tag{XIa}$$

in which

G is in each case independently, and independently of $R^9$, absent or is oxygen, and the $R^9$ radicals are in each case independently $C_1$–$C_8$-alkyl or unsubstituted, mono-, di- or tri-$R^{10}$-substituted phenyl, naphthyl or ferrocenyl, where $R^{10}$ is $C_1$–$C_8$-alkyl, $C_1$–$C_8$-alkoxy, chlorine, fluorine, $N(C_1$–$C_6$-alkyl$)_2$, $CO_2$—$(C_1$–$C_6$-alkyl), —CON$(C_1$–$C_6$-alkyl$)_2$, cyano or $CO(C_1$–$C_6$-alkyl).

Particularly preferred monophosphorus compounds are those of the formula (XIa) in which G is absent and $R^9$ is in each case independently $C_1$–$C_8$-alkyl or unsubstituted, mono-, di- or tri-$R^{10}$-substituted phenyl or naphthyl or ferrocenyl, where $R^{10}$ is $C_1$–$C_8$-alkyl, $C_1$–$C_8$-alkoxy, chlorine or fluorine.

Even greater preference is given to the monophosphorus compounds being triphenylphosphine, phenyldi(tert-butyl)phosphine and tri(tert-butyl)phosphine.

Diphosphorus compounds may be, for example and with preference, those of the formula (XIb):

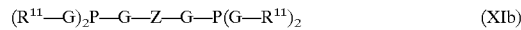

$$(R^{11}-G)_2P-G-Z-G-P(G-R^{11})_2 \tag{XIb}$$

in which

G is in each case independently, and independently of $R^{11}$ and Z, absent or is oxygen and the $R^{11}$ radicals are each independently $C_1$–$C_8$-alkyl or unsubstituted, mono-, di- or tri-$R^{12}$-substituted phenyl, naphthyl or heteroaryl having 5 to 12 framework carbon atoms, where $R^{12}$ is in each case independently selected from the group of $C_1$–$C_8$-alkyl, $C_1$–$C_8$-alkoxy, fluoro or cyano, and Z is an unsubstituted or substituted radical from the group of $C_1$–$C_4$-alkylene, 1,2-phenylene, 1,3-phenylene, 1,2-cyclohexyl, 1,1'-ferrocenyl, 1,2-ferrocenyl, 2,2'-(1,1'-binaphthyl) and 1,1'-biphenyl.

Preferred diphosphorus compounds are 1,3-bis(diisopropylphosphino)propane, 1,4-bis(diisopropylphosphino)butane, 2,2'-bis(diphenylphosphino)-1,1'-binaphthyl.

Preference is given to using complexes which contain monophosphorus compounds as ligands.

Preferred isolated palladium complexes are bis(triphenylphosphine)palladium(II) dichloride, bis-(tricyclohexylphosphine)palladium(II) dichloride, bis(di-tert-butylphenylphosphine)palladium(II) dichloride, bis(tri-tert-butylphosphine)palladium(II) dichloride, tricyclohexylphosphene-palladium(0) diallyl ether complex, bis(tricyclohexylphosphine)palladium(0) and tetrakis-(triphenylphosphine)palladium(0).

Preferred palladium catalysts for the process according to the invention are palladium complexes which are generated in the reaction solution from palladium compounds and ligands.

The palladium compounds used may be, for example and with preference: dibenzylideneacetone-palladium(0) complexes or allylpalladium chloride or bromide or those of the formula:

$$Pd(Y^1)_2 \qquad (XIIa)$$

in which $Y^1$ is an anion, preferably chloride, bromide, acetate, propionate, nitrate, methanesulphonate, trifluoromethanesulphonate, acetylacetonate, allyl or cyclopentadienyl, or palladium compounds of the formula (XIIb):

$$Pd(Y^2)_2L^3_2 \qquad (XIIb)$$

in which $Y^2$ is an anion, preferably chloride, bromide, acetate, methanesulphonate, nonafluorobutane-sulphonate, trifluoromethanesulphonate, tetrafluoroborate or hexafluorophosphate and $L^3$ is in each case a nitrile, preferably acetonitrile, benzonitrile or benzyl nitrile, or an olefin, preferably cyclohexene or cyclooctene, or $L^3_2$ together is a diolefin, preferably norbomadiene or 1,5-cyclooctadiene, or palladium compounds of the formula (XIIc):

$$M_2[Pd(Y^3)_4] \qquad (XIIc),$$

where $Y^3$ is a halide, preferably chloride or bromide and

M is lithium, sodium, potassium, ammonium or organic ammonium.

Preferred palladium compounds are palladium(II) acetate, palladium(II) chloride, palladium(II) bromide, palladium(II) propionate, palladium(II) acetylacetonate, lithium, sodium or potassium tetrachloropalladate, bis(benzonitrile)palladium(II) chloride, bis(acetonitrile)palladium(II) chloride.

For the generation of palladium complexes in the reaction solution, ligands used are preferably phosphorus compounds of the formulae (XIa) and (XIb), and even greater preference is given to monophosphorus compounds of the formula (XIa). The areas of preference specified apply in the same manner.

The molar ratio of phosphorus to palladium in the reaction mixture may be, for example, 1:1 to 10:1, preferably 2:1 to 5:1, more preferably 3:1 to 4:1.

For the process according to the invention, the molar ratio of compounds of the formula (IV) to palladium may be, for example, 10 to 20000, preferably a ratio of 100 to 5000, most preferably 500 to 2000.

The reactions which are carried out in the presence of catalyst in accordance with the invention are preferably carried out in the presence of at least one, preferably one, base.

Suitable bases are, for example, amines of the formula (XIII):

$$NH_m(R^{13})_{(3-m)} \qquad (XIII)$$

in which m is zero, one or two and the $R^{13}$ radicals are each independently $C_1$–$C_{12}$-alkyl, $C_5$–$C_{14}$-aryl or $C_6$–$C_{15}$-arylalkyl, or each case two or three of the $R^{13}$ radicals together with the nitrogen atom may form a mono-, bi- or tricyclic heterocycle having 4 to 8 carbon atoms per cycle.

Also suitable as bases are N-heteroaromatic compounds. These are, for example, optionally substituted pyridines, in particular pyridine, 2,6-bis(diisopropyl)pyridine and dimethylamino-pyrdine.

Also suitable as bases are, for example, alkali metal and/or alkaline earth metal salts of aliphatic or aromatic carboxylic acids such as acetates, propionates and benzoates, and/or carbonates, for example sodium carbonate and potassium carbonate, hydrogencarbonates, for example sodium hydrogencarbonate and potassium hydrogencarbonate, phosphates, hydrogenphosphates and/or hydroxides, for example sodium hydroxide or potassium hydroxide.

Very particularly preferred bases are diethylamine, triethylamine, ethyldiisopropylamine, di-n-propylamine, tri-n-propylamine, diisopropylamine, triisopropylamine, diisobutylamine, triisobutylamine, dicyclohexylamine, dicyclohexylmethylamine, cyclohexyldimethylamine and 2,6-bis(diisopropyl)pyridine. Particular preference is given to diethylamine and triethylamine for the conversion of alkines, and to ethyldiisopropylamine, dicyclohexylmethylamine and cyclohexyl-dimethylamine for the conversion of alkenes.

The molar amount of the base used is uncritical and may be, for example, 1 to 200 times, preferably 1 to 3 times and even more preferably 1.0 to 1.2 times, the molar amount of the compound of the formula (IV) or (VII). Bases which are liquid under the reaction conditions can also be used as a solvent.

In conversions of alkines which are carried out in the presence of catalyst in accordance with the invention, preference is given to also using copper salts, in particular copper(I) and copper(II) salts.

The anions of these salts may be halides, pseudohalides, carboxylates, perfluoroalkylsulphonates, sulphates, nitrates, carbonates, hydroxides.

Preferred halides and pseudohalides are fluoride, chloride, bromide, iodide, cyanide, cyanate, thiocyanate, preferred carboxylates are acetate and propionate, and preferred perfluoroalkyl-sulphonates are triflate and nonaflate.

Preference is also given to thioether, phosphite and phosphine adducts to copper(I) salts.

Particularly preferred copper salts are copper(I) iodide, copper(1) bromide, copper(I) chloride and copper(I) bromide-dimethyl sulphide complex.

The copper salt can be used, for example, in amounts of 0.01 to 100 mol %, based on the compounds of the formula (VII), preferably in amounts of 0.1 to 20 mol % and more preferably in amounts of 0.5 to 5 mol %. It is also possible to use combinations of a plurality of salts.

The reactions which are carried out in the presence of catalyst in accordance with the invention are optionally carried out in the presence of organic solvent, preferably in the presence of aprotic solvent, more preferably in the presence of polar aprotic solvent. The above definitions of aprotic and polar apply correspondingly.

Particularly suitable solvents are ethers, for example dioxane, THF, 1,2-dimethoxyethane, diethylene glycol dimethyl ether, tetraethylene glycol dimethyl ether, amidic solvents, for example dimethylformamide, N-methylpyrrolidone, N-methylcaprolactam or dimethylacetamide, sulphoxides and sulphones, for example dimethyl sulphoxide or tetramethylenesulphone, nitriles, for example acetonitrile, benzonitrile and benzyl nitrile, and ketones, for example dimethyl ketone, diethyl ketone, methyl tert-butyl ketone.

The reaction temperature may be, for example, 0° C. to 200° C., preferably 50 to 150° C. and more preferably 50° C. to 100° C., and the reaction pressure, for example, 0.2 to 100 bar. Preference is given to ambient pressure.

The catalytic reactions are carried out preferably but not obligatorily under a protective gas atmosphere with substantial exclusion of oxygen and moisture. Useful protective gases are, for example, nitrogen and noble gases, for example argon, or mixtures of such gases.

In a preferred embodiment of the process according to the invention, a reaction vessel is initially charged with the unsaturated compounds, the halogen compounds to be coupled, base, optionally copper salt, ligand and palladium compound, optionally with solvent, under protective gas and the mixture is heated with stirring to the reaction temperature. On completion of reaction, the mixture is poured onto water. Solid products then precipitate out and can be filtered off with suction and washed, for example with water. Liquid products can be extracted with an organic, water-miscible or sparingly water-miscible solvent, and worked up, for example distillatively. Solid products may optionally be further purified, for example, by recrystallization or reprecipitation.

It may be advantageous to carry out the reaction with controlled metering. Controlled metering means that at least one component selected from unsaturated compounds, halogen compounds to be coupled and palladium compounds is metered in in the course of the reaction.

It may also be advantageous to add free radical inhibitors, for example 2,6-di-tert-butylphenol, to the reaction mixture in catalytic reactions, in order to very substantially prevent undesired side reactions.

In the inventive manner, the compounds of the formula (I) are obtained in good yields.

The compounds of the formula (I) which can be prepared in accordance with the invention, and also the compounds of the formulae (IV), (VI), (VIa) and (VII) are suitable in particular for use in a process for preparing agrochemicals. Preferred agrochemicals are those which are used as insecticides and acaricides. These are in particular those which are specified in EP-A 571 326 and EP-A 1 219 173.

The advantage of the process according to the invention lies in its ease of performability and the good yields of pyrazolylarylalkines.

EXAMPLES

Example 1

Preparation of 1,5-dimethyl-3-trifluoromethyl-1H-pyrazole 187 ml (1.32 mol) of trifluoroacetic anhydride are added dropwise to a solution of 95.4 g (1.32 mol) of isopropenyl methyl ether in 265 ml of tert-butyl methyl ether and 107 ml (1.32 mol) of pyridine at a temperature of 0° C. to +5° C. After a reaction time of 30 min at +5° C., the reaction mixture is washed with 400 ml of water and 200 ml of a saturated $Na_2CO_3$ solution. The organic phase is removed and dried over $MgSO_4$. The solution is cooled to a temperature of −20° C. and 70.4 ml (1.32 mol) of methylhydrazine are added dropwise thereto. The reaction mixture is allowed to gradually come to room temperature, the organic phase is dried over $MgSO_4$, and the solution is subsequently concentrated under reduced pressure. Distillation of the oily residue results in 186 g (1.13 mol; 83%) of 1,5-dimethyl-3-trifluoromethyl-1H-pyrazole (b.p.: 71° C./12 mbar).

Example 2

Preparation of 4-bromo-1,5-dimethyl-3-(trifluoromethyl)-1H-pyrazole

A total of 61.9 g (388 mmol) of bromine are added dropwise at 0° C. within 2.5 h to a suspension of 60 g (366 mmol) of 1,5-dimethyl-3-trifluoromethyl-1H-pyrazole and 30.0 g (366 mmol) of anhydrous sodium acetate in 600 ml of $CHC_{13}$. On completion of addition, the mixture is allowed to come to 20° C. and is stirred for a further 4 d. After the end of the reaction, the mixture is washed with 30% $NaHCO_3$ solution, the aqueous phase is further extracted twice using 200 ml of $CHC_{13}$ each time and the combined organic phases are dried over $MgSO_4$ and concentrated. Recystallization results in 70.6 g (291 mmol, 80%) of 4-bromo-1,5-dimethyl-3-(trifluoromethyl)-1H-pyrazole as a bright yellow solid.

Example 3

Preparation of 4-ethenyl-1,5-dimethyl-3-(trifluoromethyl)-1H-pyrazole 10.0 g (41.2 mmol) of 4-bromo-1,5-dimethyl-3-(trifluoromethyl)-1H-pyrazole, 92.4 mg (0.41 mmol) of palladium acetate and 302 mg (0.82 mmol) of tetra-n-butylammonium bromide are weighed into the glass insert of an autoclave together with 366 mg (1.65 mmol) of di(tert-butyl)phenylphosphine, 8.84 g (45.3 mmol) of dicyclohexylmethylamine and dimethylacetamide (34.3 ml), and placed under a protective gas atmosphere. Subsequently, 30 bar of ethylene are injected at 20° C. and the reaction mixture is stirred at 130° C. for 30 h. After the end of the reaction, the mixture is cooled, poured onto cold dilute hydrochloric acid and extracted with $CH_2C_{12}$. The combined organic phases which have been dried over magnesium sulphate are concentrated. The product is obtained as a brown oil in an 83% yield.

Example 4

Preparation of 4-(1,2-dibromoethyl)-1,5-dimethyl-3-(trifluoromethyl)-1H-pyrazole A total of 5.73 g (35.9 mmol) of bromine are added dropwise at 0° C. within 0.5 h to a solution of 7.50 g (34.2 mmol) of 4-ethenyl-1,5-dimethyl-3-(trifluoromethyl)-1H-pyrazole in 100 ml of $CHC_{13}$. On completion of addition, the mixture is allowed to come to 20° C. and is stirred at this temperature for a further 20 h. To complete the reaction, a further 1.20 g (7.51 mmol) of bromine are added dropwise and the mixture is stirred at 50° C. for a further 48 h. After the end of the reaction, the mixture is washed with 30% $NaHCO_3$ solution, the aqueous phase is further extracted twice with 50 ml of CHC$_{13}$ each time and the combined organic phases are dried over MgSO$_4$ and concentrated. 7.3 g (20.9 mmol, 61%) of 4-(1,2-dibromoethyl)-1,5-dimethyl-3-(trifluoromethyl)-1H-pyrazole are obtained as a red-brown oil.

Example 5

Preparation of 4-ethinyl-1,5-dimethyl-3-(trifluoromethyl)-1H-pyrazole 7.3 g (20.9 mmol) of 4-(1,2-dibromoethyl)-1,5-dimethyl-3-(trifluoromethyl)-1H-pyrazole are taken up in 5 ml of toluene and heated to 70° C. for 12 h together with a 60% aqueous KOH solution (10 ml) and 1.2 g of polyethylene glycol 600. After the end of the reaction, the two phases are separated, the aqueous phase is extracted with toluene and the combined organic phases are dried over MgSO$_4$ and concentrated. The product is obtained as a solid in an 81% yield.

Example 6

Preparation of 4-(2-chloroethenyl)-1,5-dimethyl-3-(trifluoromethyl)-1H-pyrazole 2.00 g (8.23 mmol) of 4-bromo-1,5-dimethyl-3-(trifluoromethyl)-1H-pyrazole, 18.5 mg (0.08 mmol) of palladium acetate and 60.3 mg (0.165 mmol) of tetra-n-butylammonium bromide are weighed into the glass insert of an autoclave together with 73.2 mg (0.329 mmol) of di(tert-butyl)phenylphosphine, 1.77 g (9.05 mmol) of dicyclohexylmethylamine, 9.1 mg (0.082 mmol) of hydroquinone and dimethylacetamide (22.8 ml), and placed under a protective gas atmosphere. Subsequently, 2.57 g (41.2 mmol) of vinyl chloride are metered in at 20° C. and the reaction mixture is stirred at 130° C. for 30 h. After the end of the reaction, the mixture is cooled, poured onto cold, dilute hydrochloric acid and extracted with CH$_2$C$_{12}$. The combined organic phases which have been dried over magnesium sulphate are concentrated. The product is obtained as a solid in a 69% yield.

Example 7

Preparation of 4-ethinyl-1,5-dimethyl-3-(trifluoromethyl)-1H-pyrazole 1.27 g (5.67 mmol) of 4-(2-chloroethenyl)-1,5-dimethyl-3-(trifluoromethyl)-1H-pyrazole are dissolved in 40 ml of dry THF and placed under a protective gas atmosphere. After the reaction solution has been cooled to 0° C., 1.91 g (17.0 mmol) of potassium tert-butoxide are introduced and, on completion of addition, the mixture is stirred at 20° C. for 3 h. After the end of the reaction, a saturated NH$_4$Cl solution (25 ml) is added and extraction is effected twice with CH$_2$C$_{12}$. The combined organic phases are dried over MgSO$_4$ and concentrated. The product is obtained as a solid in a 79% yield.

Example 8

Preparation of 4-ethinyl-1,5-dimethyl-3-(trifluoromethyl)-1H-pyrazolyl-3,5-bis(trifluoromethyl)benzene 183 mg (0.983 mmol) of 4-ethinyl-1,5-dimethyl-3-(trifluoromethyl)-1H-pyrazole, 2.3 mg (0.01 mmol) of palladium acetate and 3.9 mg (0.02 mmol) of copper(I) iodide are weighed into a round-bottom flask and placed under protective gas. Subsequently, 9.1 mg (0.04 mmol) of di(tert-butyl)phenylphosphine, 300 mg (1.03 mmol) of 3,5-bis(trifluoromethyl)bromobenzene, 137 mg (1.08 mmol) of cyclohexyldimethylamine and dimethylacetamide (5 ml) are added and the mixture is heated to 110° C. for 12 h. After the end of the reaction, the mixture is cooled, poured onto cold, dilute hydrochloric acid and extracted with ether. The combined ether phases which have been dried over MgSO$_4$ are concentrated. The product is obtained as a solid in an 85% yield.

Example 9

Preparation of 4-ethenyl-1,5-dimethyl-3-(trifluoromethyl)-1H-pyrazolyl-3,5-bis(trifluoromethyl)benzene 10 g of 3,5-bis(trifluoromethyl)bromobenzene are mixed with 11 ml of cyclohexyldimethylamine and 30 ml of dimethylacetamide and degassed. 38 mg of palladium acetate and 152 mg of di(tert-butyl)phenylphosphine are dissolved in 5 ml of dimethylacetamide and added to the mixture. The mixture is transferred to an autoclave and 30 bar of ethylene are injected. The mixture is then heated to 110° C. and stirred at this temperature for 3 hours. At the end of the reaction, the mixture is cooled and the pressure released. Subsequently, 8.3 g of 1,5-dimethyl-3-trifluoromethyl-1H-pyrazole are added to the reaction mixture and the mixture is heated to 130° C. for 12 h. Afterwards, the mixture is cooled, added to water and worked up with toluene. Yield over the two steps: 10.5 g (76%) of slightly brownish solid.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. Process for preparing compounds of the formula (I):

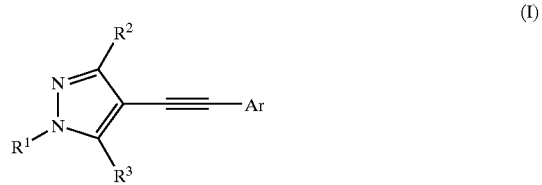

(I)

in which

R$^1$ is hydrogen, C$_1$–C$_{12}$-alkyl, C$_5$–C$_{14}$-aryl, C$_6$–C$_{15}$-arylalkyl, C$_1$–C$_{12}$-fluoroalkyl or radicals of the formula (II):

(II)

and

R$^2$ and R$^3$ are each independently hydrogen, C$_1$–C$_{12}$-alkyl, C$_1$–C$_{12}$-alkoxy, C$_5$–C$_{14}$-aryl C$_5$–C$_{14}$-aryloxy, C$_6$–C$_{15}$-arylalkyl, C$_6$–C$_{15}$-arylalkoxy, chlorine, fluorine, cyano, free or protected formyl, C$_1$–C$_{12}$-fluoroalkyl, C$_1$–C$_{12}$-fluoroalkylthio, C$_1$–C$_{12}$-fluoroalkoxy or radicals of the formulae (IIIa) to (IIIf):

| | | | | |
|---|---|---|---|---|
| A—B—D—E | (IIIa) | A—E | (IIIb) | |
| A—SO$_2$—E | (IIIc) | A—B—SO$_2$R$^5$ | (IIId) | |
| A—SO$_3$W | (IIIe) | A—COW | (IIIf) | | where, in the formulae (II) and (IIIa) to (IIIf),

A is absent or is a $C_1$–$C_8$-alkylene, $C_1$–$C_8$-alkenylene or $C_1$–$C_8$-fluoroalkylene radical and B is absent or is oxygen, sulphur or NR$^4$ where R$^4$ is hydrogen, $C_1$–$C_8$-alkyl, $C_6$–$C_{15}$-arylalkyl or $C_5$–$C_{14}$-aryl and D is a carbonyl group and E is R$^5$, OR$^5$, NHR$^6$ or N(R$^6$)$_2$, where R$^5$ is $C_1$–$C_8$-alkyl, $C_6$–$C_{15}$-arylalkyl or $C_5$–$C_{14}$-aryl and R$^6$ is in each case independently $C_1$–$C_8$-alkyl, $C_6$–$C_{15}$-arylalkyl or $C_6$–$C_{14}$-aryl, or N(R$^6$)$_2$ together is a cyclic amino radical having 4 to 12 carbon atoms and W is OH, NH$_2$ or OM where M is an alkali metal ion, half an equivalent of an alkaline earth metal ion, an ammonium ion or an organic ammonium ion and Ar is a mono-, bi- or tricyclic aromatic radical having a total of 5 to 18 ring atoms, and in which at most one ring atom per cycle is selected from the group of oxygen, sulphur and nitrogen, and the mono-, bi- or tricyclic aromatic radical is optionally mono- or polysubstituted, comprising:

in step a), reacting the compounds of the formula (IV):

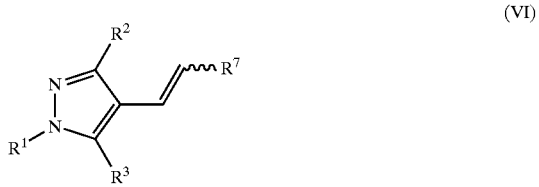

(IV)

in which

R$^1$, R$^2$ and R$^3$ are each independently as defined above and

Hal is chlorine, bromine or iodine with compounds of the formula (V):

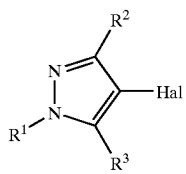

(V)

in which

R$^7$ is hydrogen, halogen, Ar or COOR$^8$ where

R$^8$ is $C_1$–$C_8$-alkyl, $C_5$–$C_{14}$-aryl or $C_6$–$C_{15}$-arylalkyl, in the presence of a catalyst, to convert them to compounds of the formula (VI):

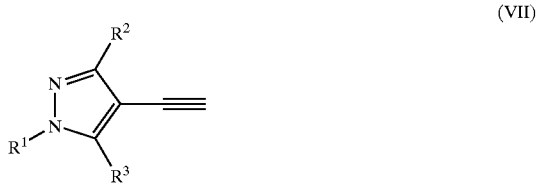

(VI)

in which

R$^1$, R$^2$, R$^3$ and R$^7$ are each independently as defined above and in step b), I) in the case that R$^7$ is hydrogen, halogen or COOR$^8$,
  i) converting the compounds of the formula (VI), optionally after halogenation, by elimination to compounds of the formula (VII):

(VII)

in which

R$^1$, R$^2$ and R$^3$ are each independently as defined above and ii) reacting the compounds of the formula (VII) with compounds of the formula (VII):

Hal-Ar  (VIII)

in which

Ar is as defined above and Hal is chlorine, bromine or iodine, in the presence of a catalyst to produce the compounds of formula (I), II) and in the case that R$^7$ is Ar, the compounds of the formula (VI) are converted to compounds of the formula (I) by halogenating and eliminating.

2. Process according to claim 1, characterized in that R$^1$ is hydrogen, phenyl or $C_1$–$C_4$-alkyl.

3. Process according to claim 1, characterized in that R$^2$ is $C_1$–$C_{12}$-fluoroalkyl.

4. Process according to claim 1, characterized in that R$^3$ is hydrogen, $C_1$–$C_4$-alkyl, $C_5$–$C_{14}$-aryl or radicals selected from the group consisting of:
—CH$_2$COO($C_1$–$C_8$-alkyl), —CH$_2$COO($C_5$–$C_{14}$-aryl), —CH$_2$CONH($C_1$–$C_8$-alkyl), —CH$_2$CON($C_1$C$_{18}$-alkyl)$_2$, —C(=CHOCH$_3$)COO($C_1$–$C_8$-alkyl), C(=CHOCH$_3$)COO($C_5$–$C_{14}$-aryl), —C(=CHOCH$_3$)CONH($C_1$–$C_8$-alkyl), and —C(=CHOCH$_3$)CON($C_1$–$C_8$-alkyl)$_2$.

5. Process according to claim 1, characterized in that Ar is a phenyl or pyridyl radical which is non-, mono-, di- or trisubstituted by radicals which are selected from the group consisting of chlorine, fluorine, $C_1$–$C_{12}$-alkyl, $C_1$–$C_{12}$-fluoroalkyl, $C_1$–$C_{12}$-fluoroalkoxy, $C_1$–$C_{12}$-fluoroalkylthio, $C_1$–$C_{12}$-alkoxy, di($C_1$–$C_8$-alkyl)amino, tri($C_1$–$C_6$-alkyl) siloxyl and radicals of the formulae (IIIa) to (IIIf) as defined in claim 1.

6. Process according to claim 1, characterized in that R$^7$ is hydrogen, bromine, chlorine, COO-methyl, COO-ethyl, COO-phenyl, COO-isopropyl or COO-tert-butyl.

7. Process according to claim 1, characterized in that 4-ethynyl-1,5-dimethyl-3-(trifluoromethyl)-1H-pyrazolyl-3,5-bis(trifluoromethyl)benzene is prepared.

8. Process according to claim 1, characterized in that the halogenation is effected by reacting the compound of formula (VI) with bromine, chlorine or interhalogen compounds of bromine and chlorine.

9. Process according to claim 8, characterized in that the reaction temperature in the halogenation is −20 to 150° C.

10. Process according to claim 1, characterized in that eliminations are carried out in an organic solvent in the presence of base.

11. Process according to claim 10, characterized in that polar, aprotic solvents are used for the elimination.

12. Process according to claim 10, characterized in that the bases used are: alkaline earth metal or alkali metal hydrides, hydroxides, amides, alkoxides, tertiary amines or else N-heteroaromatic compounds.

13. Process according to claim 11, characterized in that the eliminations are carried out at temperatures of −20 to 200° C.

14. Process according to claim 1, characterized in that, in the case of eliminations which are preceded by a halogenation, an intermediate isolation and/or purification of the intermediates is dispensed with.

15. Process according to claim 1, characterized in that the reactions in the presence of catalysts.

16. Process according to claim 1, characterized in that the catalysts used are those which contain palladium.

17. Process according to claim 16, characterized in that palladium complexes are used.

18. Process according to claim 17, characterized in that the palladium complexes used are palladium complexes which have already been isolated or those which are generated in the reaction solution from palladium compounds and ligands.

19. Process according to claim 16, characterized in that the molar ratio of halogen compound to be coupled to palladium is 10 to 20000.

20. Process according to claim 15, characterized in that the bases used are amines of the formula (XIII):

$$NH_m(R^{13})_{(3-m)} \qquad (XIII)$$

in which m is zero, one or two and the $R^{13}$ radicals are each independently $C_1$–$C_{12}$-alkyl, $C_5$–$C_{14}$-aryl or-$C_6$–$C_{15}$-arylalkyl, or two or three of the $R^{13}$ radicals together with the nitrogen atom optionally form a mono-, bi- or tricyclic heterocycle having 4 to 8 carbon atoms per cycle or N-heteroaromatic compounds and/or alkali metal and/or alkaline earth metal salts of aliphatic or aromatic carboxylic acids and/or carbonates, phosphates, hydrogenphosphates and/or hydroxides.

21. Process according to claim 1, characterized in that the conversions of alkynes in the presence of catalyst are carried out in the presence of copper salt.

22. Process according to claim 21, characterized in that anions of the copper salts used are halides, pseudohalides, carboxylates, perfluoroalkylsulphonates, sulphates, nitrates, carbonates or hydroxides, wherein anions of the copper salts are selected form the group consisting of thioether, phosphite and phosphine adducts of copper(I) salts.

23. Process according to claim 15, characterized in that the reaction is carried out with controlled metering.

24. Process according to claim 15, characterized in that free radical inhibitors are added.

* * * * *